United States Patent
Edwards et al.

(10) Patent No.: US 7,813,594 B2
(45) Date of Patent: Oct. 12, 2010

(54) OWNERSHIP TAGGING AND DATA ASSURANCE OF IMAGE DATA SYSTEM AND METHOD

(75) Inventors: James W. Edwards, Guelph (CA); David J. Ferraro, Waterloo (CA)

(73) Assignee: Agfa Inc., Toronto (CA)

( * ) Notice: Subject to any disclaimer, the term of this patent is extended or adjusted under 35 U.S.C. 154(b) by 971 days.

(21) Appl. No.: 11/638,485

(22) Filed: Dec. 14, 2006

(65) Prior Publication Data

US 2008/0147860 A1    Jun. 19, 2008

(51) Int. Cl.
*G06K 9/54* (2006.01)
*G06K 9/173* (2006.01)

(52) U.S. Cl. .......................... 382/305; 709/225
(58) Field of Classification Search ................ 382/128, 382/305, 312; 709/203, 223, 225, 232; 707/104.1, 707/204; 600/407, 426, 300; 713/400; 705/2; 623/17.16
See application file for complete search history.

(56) References Cited

U.S. PATENT DOCUMENTS

| | | | |
|---|---|---|---|
| 5,642,513 A * | 6/1997 | Schnellinger et al. ....... | 717/141 |
| 6,574,742 B1 * | 6/2003 | Jamroga et al. ............. | 713/400 |
| 7,574,452 B2 * | 8/2009 | Keen ........................ | 707/104.1 |
| 2005/0196030 A1 * | 9/2005 | Schofield et al. ............ | 382/132 |
| 2006/0112188 A1 * | 5/2006 | Albanese et al. ............ | 709/238 |
| 2006/0122482 A1 * | 6/2006 | Mariotti et al. ............. | 600/407 |
| 2006/0224619 A1 * | 10/2006 | Kang et al. ................ | 707/103 X |
| 2007/0106710 A1 * | 5/2007 | Haustein et al. ............. | 707/204 |
| 2007/0237402 A1 * | 10/2007 | Dekel et al. ................. | 382/232 |
| 2007/0299945 A1 * | 12/2007 | Lunsford .................... | 709/223 |
| 2008/0016240 A1 * | 1/2008 | Balandin .................... | 709/238 |
| 2008/0046538 A1 * | 2/2008 | Susarla et al. ............... | 709/217 |

* cited by examiner

*Primary Examiner*—Kanji Patel
(74) *Attorney, Agent, or Firm*—Bereskin & Parr LLP; Isis E. Caulder

(57) ABSTRACT

A system and method for managing the archival and retention of data in a multiple-node PACS network. Data is distributed among network nodes such that a secondary node will not delete a received image study it has received from a primary node if the primary node is an originating source. Instead, the secondary node will execute data retention. Data retention is achieved by including a delete retention attribute within the metadata associated with the received image data on the secondary node and requiring that the secondary node enforce data retention if a data retention attribute is identified within the metadata stored on the secondary node.

15 Claims, 4 Drawing Sheets

OWNERSHIP TAGGING AND DATA ASSURANCE OF IMAGE DATA SYSTEM AND METHOD

FIELD

The embodiments described herein relate to a system and method for image storage and more particularly to a system and method for assuring archiving and retention of medical diagnostic images.

BACKGROUND

Medical imaging has been an expanding field for several decades. With increasing diagnostic tools, increasing population, more widespread access to medical treatment, and the desirability of sharing information between doctors and professionals, medical imaging is very likely to continue growing at a rapid rate. To address this continued growth, and the subsequent inconveniences of paper and other fixed forms of medical image storage, the medical community has increasingly turned to digital forms of image storage.

Picture Archiving and Communications Systems (PACS) are a common example of a digital image system. These systems connect elements such as imaging modalities, storage databases or areas, clients that use the medical image data, and data processing devices to create a network of imaging technology. Such systems then provide easier remote diagnosis and data access, sharing of information between health-care professionals, and ultimately a better health-care system.

Currently, large volume Computed Tomography (CT), Magnetic Resonance (MR) and X-Ray Angiography (XA) DICOM studies acquire a large number of image data files that must be transferred within and between local PACS networks. A typical image dataset can easily contain over 2000 slices that translates into a similar number of image data files.

Enterprise Picture Archiving and Communication Systems (PACS) deployments, such as those found in a hospital, provide a centralized means of searching, retrieving and storing images using the Digital Imaging and Communications in Medicine (DICOM) protocol. Key to the concept of a PACS is the archiving component. Using the underlying principle of time-based or rules-based storage, acquired DICOM objects such as images are kept on long-term media for retrieval at a later time, through a centralized location. Images may be stored on a variety of media, including but not limited to Magneto-Optical Disc (MOD), Digital Linear Tape (DLT), Compact Disc (CD) or Digital Versatile Disc (DVD).

Accordingly, medical images may have been transmitted from multiple locations within a hospital. Often, the originating source of the image, while referenced in the DICOM metadata, may not have been the last known sender of the medical image. This downstream mechanism presents a dilemma in multiple-node PACS deployments when it is desired to delete an image study from a particular PACS.

It may be desirable to delete an image study for reasons of storage space conservation. Another reason is the practical difficulties associated with maintaining duplicates of an image study. For example, the DICOM standard requires that each medical image should have a unique identifier (known as the sop_instance_uid). Also, some PACS implementations will refuse to accept duplicate medical images. As such, it may be necessary to delete the medical image study in order to enable a retransmission. If an image study transmission has resulted in data corruption due to external influences (media, network, etc), then a manual deletion may become necessary.

At the same time, image data retention and integrity is highly desirable and generally speaking, an imaging study should not be deleted if it is not available on another PACS within the network. However, the final archive destination may not be the initial PACS accepting the image data. There is currently no adequate means of verifying that a particular imaging study is safe to delete (i.e., stored elsewhere). Thus, it is desirable to provide a means of assurance for study, series, image and object persistence and availability in a multiple-node PACS environment.

SUMMARY

The embodiments described herein provide in one aspect, a system for archiving and retention of image data within a multiple node image storage network, said system comprising:
  (a) a primary network node for storing and sending transmitted image data, where said transmitted image data includes metadata;
  (b) a secondary network node coupled to the primary network node for receiving and storing the transmitted image data as received image data, where said received image data includes metadata,
  (c) said secondary network node also including a data protection module configured for:
    (i) determining whether the primary network node is the originating source of the image data;
    (ii) if (i) is true, then including a data retention attribute within the metadata for the received image data stored on the secondary network node; and
    (iii) reading the metadata on the secondary network node and enforcing data retention if the metadata includes a data retention attribute.

The embodiments described herein provide in another aspect, a method for archiving and retention of image data within a multiple node image storage network having primary and secondary network nodes, said method comprising:
  (d) storing transmitted image data on the primary network node and sending transmitted image data to the secondary node, where said transmitted image data includes metadata;
  (e) receiving and storing the transmitted image data as received image data on the secondary network note, where said received image data includes metadata,
  (f) determining whether the primary network node is the originating source of the image data;
  (g) if (c) is true, then including a data retention attribute within the metadata for the received image data stored on the secondary network node; and
  (h) reading the metadata on the secondary network node and enforcing data retention if the metadata includes a data retention attribute.

Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

Figure 1:
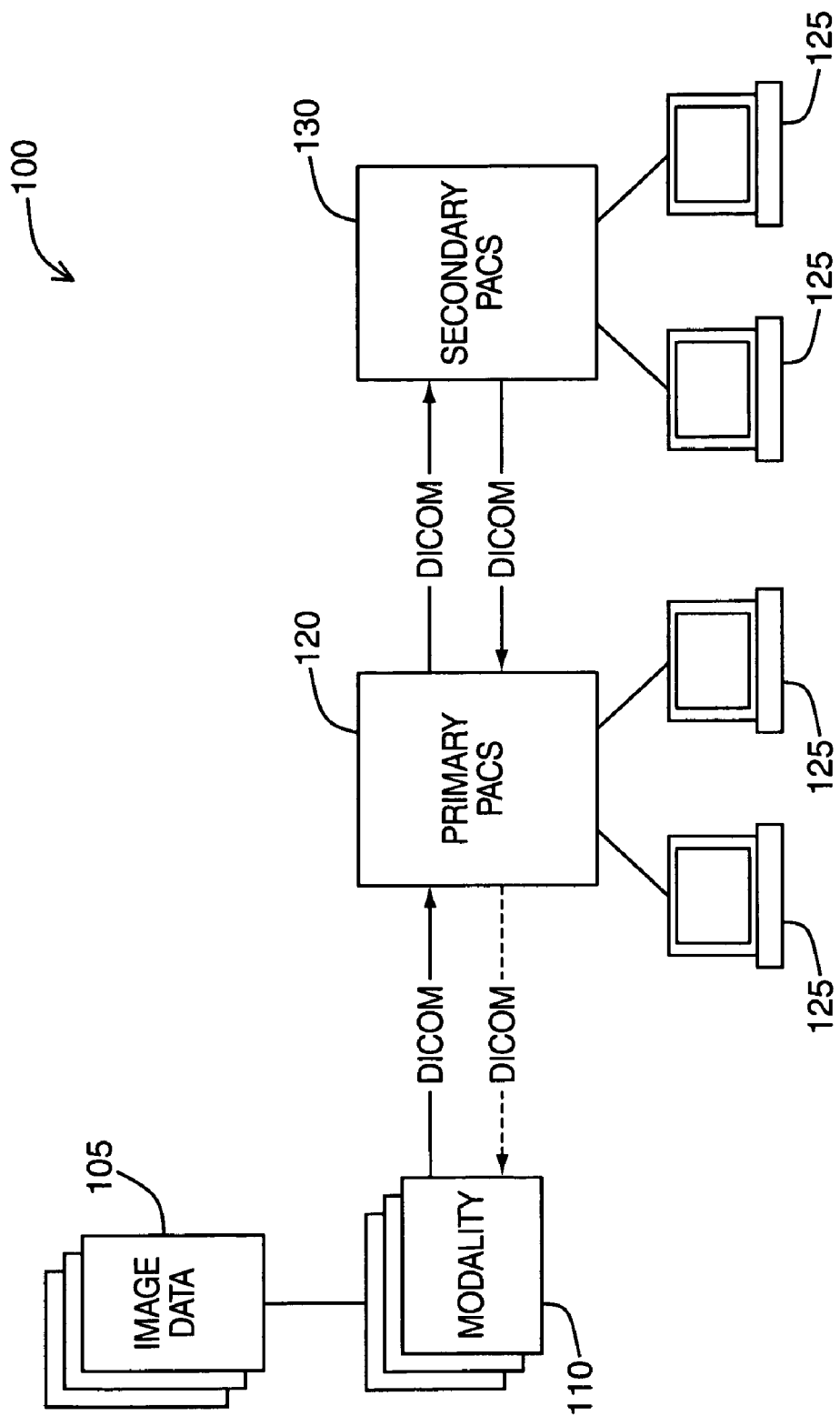
FIG. 1 is a block diagram of a two-node PACS network.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), at least one input device, and at least one output device. For example and without limitation, the programmable computers may be a personal computer, laptop, personal data assistant, and cellular telephone. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Reference is first made to FIG. 1, which is a block diagram illustrating an exemplary embodiment of a two-node PACS network 100. As shown, image data 105 is acquired by a number of imaging modalities 110. Image data is then transferred to a primary PACS 120, using a communication protocol, such as one of the DICOM communication protocols. In a typical DICOM communication exchange, one of the modality 110 and the primary PACS 120 will act as a Service Class User (SCU), while the other acts as a Service Class Provider (SCP). The SCU is designed as a mechanism to send data objects, including image data objects, to a DICOM compliant listener. This listener, as an SCP, receives the object and is able to identify the enclosed metadata (e.g., modality, patient information) within that image data object.

Modality 110 may request to store image data 105 on primary PACS 120 or, alternately, primary PACS 120 may request image data from modality 110. In response to the request, the device currently storing the image data 105 sends the image data 105 over a communications channel using an appropriate communication protocol, such as DICOM SCU/SCP. Optionally, the receiving device may acknowledge receipt using an additional communication protocol.

Each image data file generated from image data 105 can be expressed as two logical parts. One part is known as pixel data that represents the displayed image. The other logical part is the metadata that represents a set of attributes that describes the image such as patient information, study grouping, and image attributes.

Once the image data is received from modality 110, users of primary PACS 120 may access the image data 105 now stored on primary PACS 120 using a workstation 125, which may be a computer workstation consisting of a processor, display device and input devices (e.g., keyboard, mouse). Alternatively, workstation 125 may be a mobile device or any other suitable access device for displaying image data.

A secondary PACS 130 may then request image data from the primary PACS 120 using a communication protocol, such as the DICOM communication protocol. In response to the request, the primary PACS 120 will commence sending the requested image data 105 over a communications channel using an appropriate communication protocol, such as DICOM SCU/SCP. Optionally, the receiving device may acknowledge receipt using an additional communication protocol.

Once the image data 105 is received from the primary PACS 120, users of the secondary PACS 130 may similarly access the image data 105 stored on the secondary PACS 130 using workstations 125.

Figure 2:
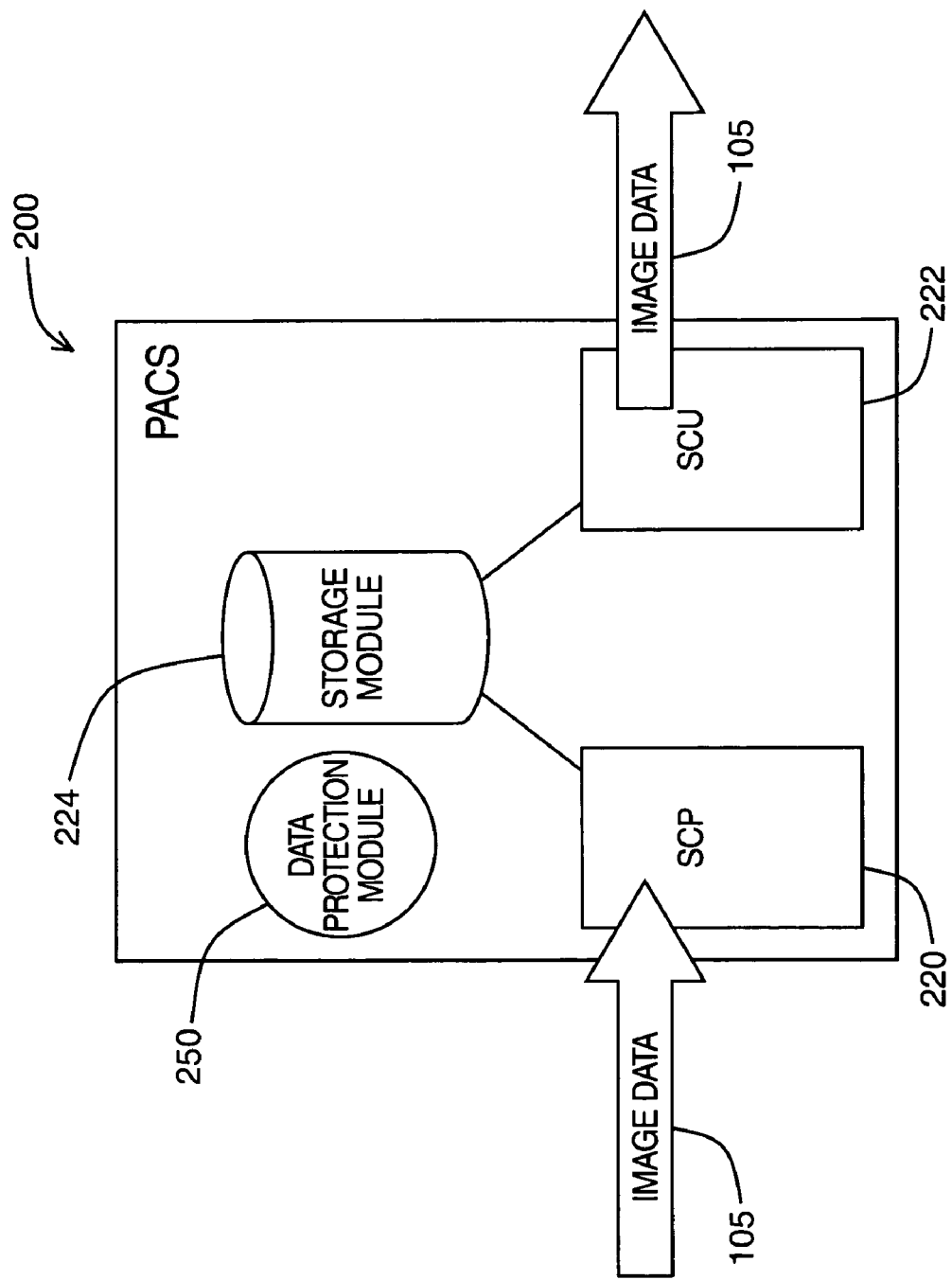
FIG. 2 is a simplified block diagram of a PACS.

Referring now to FIG. 2, there is shown a simplified block diagram representation of a PACS 200. The image data 105 is received by a Service Class Provider (SCP) 220 over a communications channel and retained in a storage module 224. In response to a request, a Service Class User (SCU) 222 may further retrieve image data 105 from the storage module 224 and send it over a communications channel.

According to one exemplary embodiment, it is possible to alter the deletion functionality on the secondary PACS 130 when the source of particular image data is identified as the primary PACS 120, rather than another modality 110. The SCP 220 on the secondary PACS 130 is generally a receiver of data from an acquisition source, which may represent itself as a modality 110. However, generally speaking, a PACS 200 is normally not the original acquisition source, but rather, a receiver and retransmission device.

It is therefore desirable to create a metadata attribute to identify a primary PACS 120 that has received the image data directly from a modality 110, and to generally prevent an attempt by the secondary PACS 130 to delete the study on the secondary PACS 130 in that situation. Specifically, the metadata attribute identifying the primary PACS 120 may make use of the "Application Entity Title" (or "AE_title") attribute in the DICOM image format. Also, the delete protection metadata attribute may take the form of a private metadata attribute, as specified in the DICOM image format.

As conventionally known, DICOM allows for the use of a private group and element tag for the purpose of implementing a proprietary or non-common information entity. Applications can be programmed to perform specific functions based on the presence and subsequent content of that non-common information entity, as needed. In the scenario above, the metadata attribute associated with the primary PACS 120 would include the primary PACS "AE_title" so that the secondary PACS 130 knows who the authoritative owner of the image study is. The primary PACS 120 would then retain the main responsibility to ensure that the image study is not deleted. The primary PACS 120 could send an update to modify this metadata attribute if the status of the image study needs to be changed to allow deletion.

In an alternative embodiment, the deletion protection may be specified in a local objects database, registry or other suitable index. If the deletion protection metadata attribute is present, the deletion protection module 250 overrides attempts by a secondary PACS 130 to delete the study on the secondary PACS 130. In one particular exemplary embodiment, a particular SQL table could be used, namely "dosr_study_location", that contains an attribute to allow/disallow local deletion. Through extension, this table can be reused to deny deletion from the non-authoritative secondary PACS 130.

The ability to implement such a tracking system within a multiple PACS environment ensures that the last PACS system that receives an image study will not delete it from its system (i.e. the study will be protected on the last PACS system to receive it).

Figure 3:
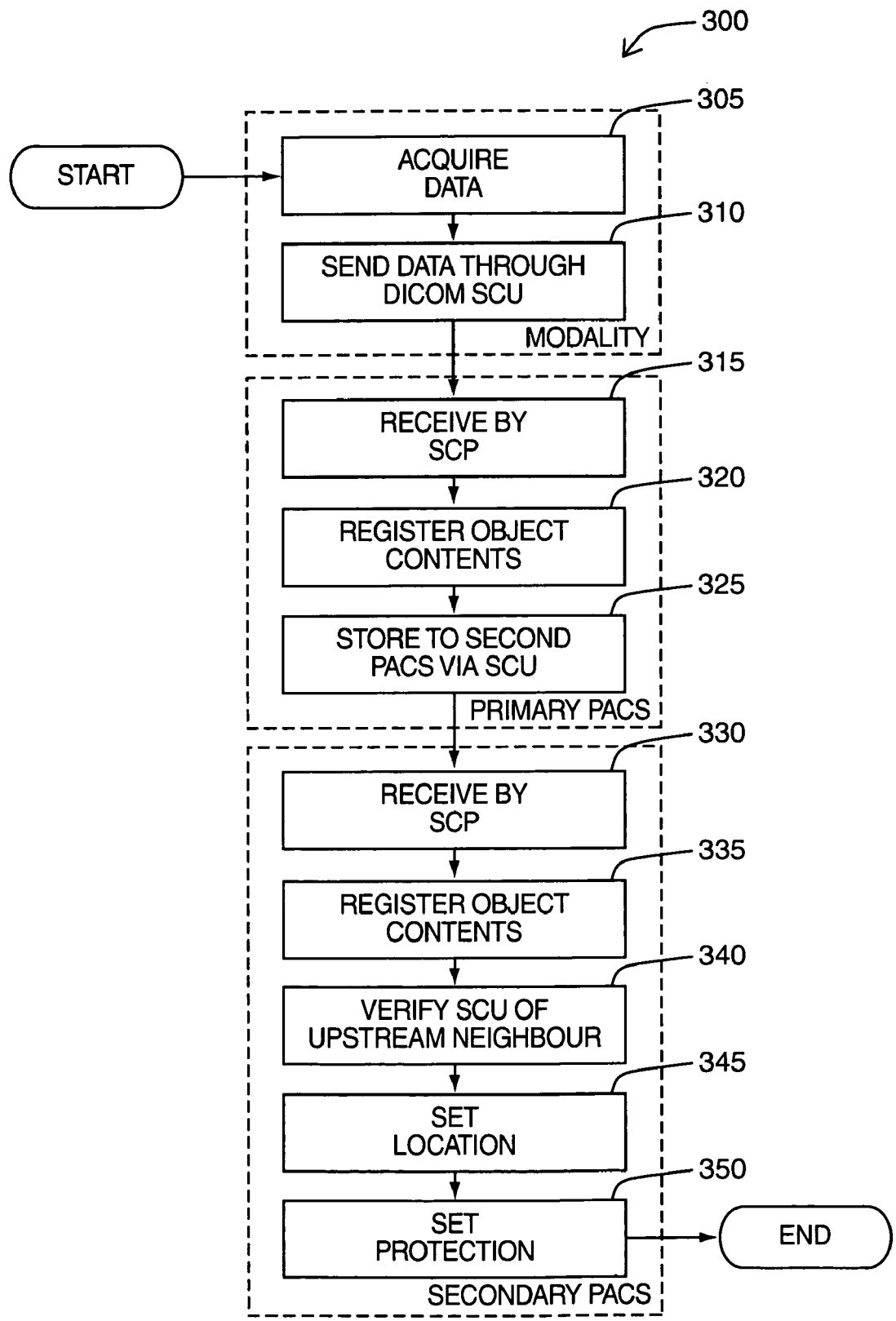
FIG. 3 is a flowchart diagram illustrating the operational steps that are executed in order for a secondary PACS to acquire image data from a modality through a primary PACS and set delete protection.

Referring now to FIG. 3, there is shown a flowchart diagram that illustrates the operational steps 300 required for a secondary PACS 130 to acquire image data 105 (i.e. an image study) from the modality 110 through the primary PACS 120 and to set the delete protection metadata attribute.

At step (305), image data 105, for example, an image study, is acquired by the modality 110. At step (310), the modality 110 sends the image study to the primary PACS 120 using a DICOM SCU 222. The image study is received by the primary PACS 120 at step (315), using the DICOM SCP 220 of the primary PACS 120. The contents of the image study are registered by the primary PACS 120 at step (320), to generate a record of the image study objects.

Next, at step (325) the image study is stored to the secondary PACS 130 using the DICOM SCU 222 of the primary PACS 120. The DICOM SCP 220 of the secondary PACS 130 receives the image study at step (330). At step (335), the contents of the image study are again registered, this time by the secondary PACS 130, to generate a local record in the storage module 224 of the image study objects.

At step (340), the secondary PACS 130 examines the DICOM "Source Calling Title" of the sending DICOM SCU 222 of the primary PACS 120 to identify that the source of the image study is an "upstream neighbor" (i.e. in this case the primary PACS 120).

An "upstream neighbor" for a particular image study should be understood to represent a network entity that is primarily responsible for keeping track of an image study and is normally considered to be the originating source PACS. A "downstream neighbor" for a particular image study is understood as representing a network entity that receives an image study from an "upstream neighbor" or an originating source PACS.

The identification of an upstream neighbor is essentially a triggering event for the enablement of the delete protection metadata attribute within the downstream neighbor. Accordingly, in the example discussed above, any transmission from a DICOM SCU 222 to the secondary PACS 130 would be considered to indicate the presence of an upstream neighbor as long as there is an expectation is that the primary PACS 120 is primarily responsible (as the originating source PACS) for keeping track of an image study and that the secondary PACS 130 will retain the image study for future retrieval.

At step (345), the database location is then set and the location setting for the image study objects in the image study is excluded. File location is normally a distinct function of the receiving SCP as defined by DICOM. Finally, at step (350), the secondary PACS 130 sets or enables the delete protection metadata attribute on the image study.

If a particular image study has the delete protection metadata attribute set or enabled, then the image study cannot be deleted. Retention is enforced by the deletion protection module 250, which operates by overriding attempts to delete the image study from a secondary PACS 130.

In a two-PACS system, the primary PACS 120 is the owner of the study (i.e. the primary PACS 120 keeps track of where it has 'stored' the image study) and the secondary PACS 130 is responsible to ensure that the image study is not deleted from its system. In this scenario, it is not necessary for the primary PACS 120 to keep a copy of the image study. Instead, the primary PACS 120 only needs to maintain a pointer to the image study on the secondary PACS 130 so that if a request is received for the image study it can retrieve the image study from the secondary PACS 130.

In an alternative embodiment, in which there are more than two PACS, this logic can be extended to apply to any number of attached PACS.

For example, in a multiple PACS system, if multiple secondary PACS 130 receive an image study from a primary PACS 120, then the primary PACS 120 would have a pointer to the image study on each of the secondary PACS 130. Also, under the presently discussed data assurance system and method, the various secondary PACS 130 would not be able to delete that particular image study. However, each secondary PACS 130 would be able to then retransmit the image study to another downstream PACS. The decision on deletion protection then of a repetitive nature, based on whether or not the secondary PACS 130 is identified as an upstream neighbor (i.e. the originating source PACS) for a tertiary PACS.

Accordingly, if the image study were subsequently retransmitted from the secondary PACS 130 to a downstream tertiary PACS, the secondary PACS 130, as an upstream neighbor, would be tagged by the tertiary PACS as the authority for deletion of the copy of that image study on the tertiary PACS. Accordingly, the tertiary PACS would see the secondary PACS 130 as the authority for deletion of the image study (i.e. the originating source PACS). In this instance, there would be a copy of the image study on both the secondary PACS 130 and the tertiary PACS. It should be understood that it is permissible in this scenario, for any downstream PACS to have both a copy and multiple pointers to the same image study on different downstream neighbor PACS.

Optionally, an administrative function is provided within the deletion protection module 250 to allow the secondary PACS 130 to override the delete protection metadata attribute, if necessary. Upon deletion through administrative access, a notification is sent to the primary PACS 120 indicating the data deletion.

Figure 4:
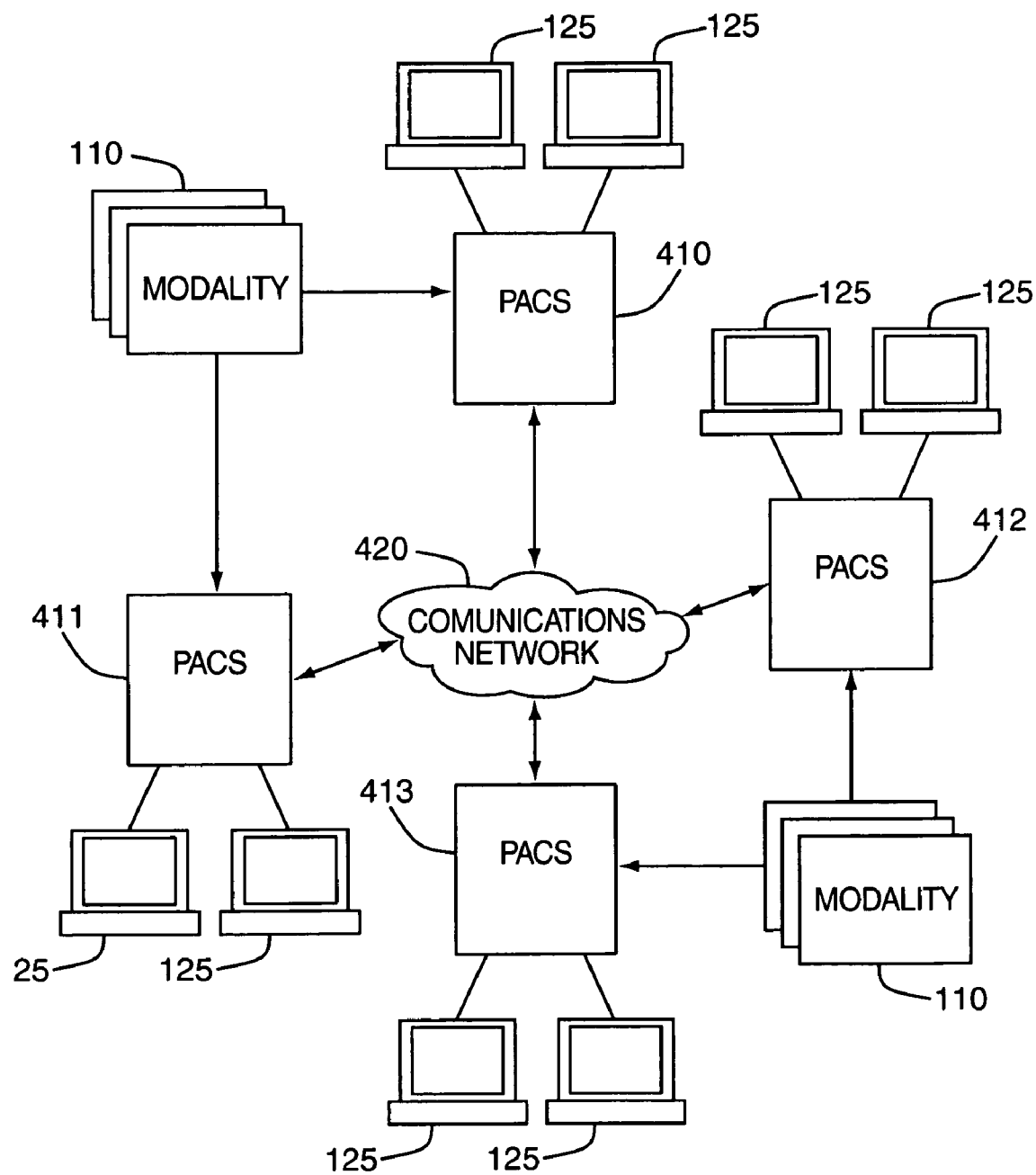
FIG. 4 is a block diagram of a multiple-node PACS network.

Referring now to FIGS. 2 and 4, there is shown a block diagram of a multiple-node PACS network. The modalities 110 acquire image data, in the form of medical image studies, which are stored in the PACS 410, 411, 412 and 413. The PACS 410, 411, 412 and 413 may exchange image studies over a communications network 420. Image studies are then reviewed by clinicians using user workstations 125, that are connected to each of the PACS 410, 411, 412 and 413.

In one scenario, image data 105 is transmitted from the SCU 222 of the PACS 410 to the SCP 220 of the PACS 411, through the communications network 420 and retained in the storage module 224 of the PACS 411. The PACS 411 verifies that the SCU 222 of the PACS 410 is an upstream neighbor (i.e., as previously discussed, the primary PACS for this image study) and therefore the delete protection metadata attribute is enabled for the image study on the PACS 411. As previously discussed, the identification of an upstream neighbor PACS is essentially a triggering event for the enablement of the delete protection metadata attribute within the downstream neighbor PACS.

Next, the PACS 412 may receive the same image data 105 from the PACS 411, following a similar procedure. However, the PACS 412 identifies that the SCU 222 of the PACS 411 is not an upstream neighbor PACS (i.e., not the originating source PACS for this twice received image study) and therefore the delete protection metadata attribute is not enabled, and the image study may safely be deleted from the PACS 412 at a later date, as it will still be protected on the "primary" PACS 411.

In another scenario, image data 105 is transmitted by the SCU 222 of PACS 410 to the SCP 220 of the PACS 411, through communications network 420 and retained in the storage module of the PACS 411. The PACS 411 verifies that the SCU 222 of the PACS 410 is an upstream neighbor PACS and therefore the delete protection metadata attribute is enabled for the study on the PACS 411. The PACS 410 updates its local database to reflect that the PACS 411 now has a copy of the image study, and the original copy of the image study may safely be deleted from the PACS 410.

Next, the PACS 412 may request the same image data 105, also from the PACS 410. However, the PACS 410 identifies that it no longer has the data and instead sends a pointer to the image data now located on the PACS 411. The PACS 412 then retrieves the data from the PACS 411, but as the PACS 411 is not the originating source, the delete protection metadata attribute for the study will not be enabled on the PACS 412.

It will be appreciated that while reference has been made to storage and protection of medical imaging studies, the same system and method may be used for other data objects which may be managed in a PACS system, whether they are studies, series patients, images or other such objects. In particular, DICOM objects, not limited to image data, may be protected according to embodiments of the invention. It will further be appreciated that while PACS networks have been described in the context of medical image management in order to provide an application-specific illustration, it should be understood that PACS networks could also be applied to any other type of image or document display system.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

The invention claimed is:

1. A system for archiving and retention of image data within a multiple node image storage network, said system comprising:
   (a) a primary network node for storing and sending transmitted image data, where said transmitted image data includes metadata;
   (b) a secondary network node coupled to the primary network node for receiving and storing the transmitted image data as received image data, where said received image data includes metadata,
   (c) said secondary network node also including a data protection module configured for:
      (i) determining whether the primary network node is the originating source of the image data;
      (ii) if (i) is true, then including a data retention attribute within the metadata for the received image data stored on the secondary network node; and
      (iii) reading the metadata on the secondary network node and enforcing data retention if the metadata includes a data retention attribute.

2. The system of claim 1, wherein data retention consists of ensuring that the received image data is not deleted from the secondary network node.

3. The system of claim 1, wherein data retention consists of ensuring that the transmitted image data is not deleted from the primary network node.

4. The system of claim 1, wherein once the data retention attribute is included within the metadata for the received image data on the secondary network node, the primary network node deletes the transmitted image data from the primary network node.

5. The system of claim 1, wherein the image storage network is a PACS network and the primary and secondary network nodes are primary and secondary PACS.

6. The system of claim 1, wherein the transmitted and received image data is medical imaging data according to the DICOM specification.

7. The system of claim 1, wherein the secondary network node is also configured to send the received image data and wherein the system further comprises a third network node coupled to the secondary network node for receiving the received image data as twice received image data, and wherein said third network node also includes a data protection module configured for:
   (iv) determining whether the secondary network node is the originating source of the image data;
   (v) if (iv) is true, then including a data retention attribute within the metadata for the twice received image data on the third network node; and
   (vi) reading the metadata on the third network node and enforcing data retention if the metadata includes a data retention attribute.

8. A method for archiving and retention of image data within a multiple node image storage network having primary and secondary network nodes, said method comprising:
   (a) storing transmitted image data on the primary network node and sending transmitted image data to the secondary network node, where said transmitted image data includes metadata;
   (b) receiving and storing the transmitted image data as received image data on the secondary network node, where said received image data includes metadata, (c) determining whether the primary network node is the originating source of the image data;

(d) if (c) is true, then including a data retention attribute within the metadata for the received image data stored on the secondary network node; and (e) reading the metadata on the secondary network node and enforcing data retention if the metadata includes a data retention attribute.

9. The method of claim 8, wherein data retention consists of ensuring that the received image data is not deleted from the secondary network node.

10. The method of claim 8, wherein data retention consists of ensuring that the transmitted image data is not deleted from the primary network node.

11. The method of claim 8, wherein once the data retention attribute is included within the metadata for the received image data on the secondary network node, the primary network node deletes the transmitted image data from the primary network node.

12. The method of claim 8, wherein the image storage network is a PACS network and the primary and secondary network nodes are primary and secondary PACS.

13. The method of claim 8, wherein the transmitted and received image data is medical imaging data according to the DICOM specification.

14. The method of claim 8, wherein the secondary network node is also configured to send the received image data and wherein the system further comprises a third network node coupled to the secondary network node for receiving the received image data as twice received image data, and further comprises:

(i) determining whether the secondary network node is the originating source of the image data;

(ii) if (i) is true, then including a data retention attribute within the metadata for the twice received image data on the third network node; and (iii) reading the metadata on the third network node and enforcing data retention if the metadata includes a data retention attribute.

15. A non-transitory computer-readable medium upon which a plurality of instructions are stored, the instructions for performing the steps of the method as claimed in claim 8.

* * * * *